United States Patent
Bedingham et al.

(10) Patent No.: US 6,245,007 B1
(45) Date of Patent: Jun. 12, 2001

(54) BLOOD PUMP

(75) Inventors: William Bedingham, Woodbury; Bernard A. Gonzalez, St. Paul; Gustavo H. Castro, Cottage Grove, all of MN (US)

(73) Assignee: Terumo Cardiovascular Systems Corporation, Somerset, NJ (US)

( * ) Notice: Subject to any disclaimer, the term of this patent is extended or adjusted under 35 U.S.C. 154(b) by 0 days.

(21) Appl. No.: 09/239,440

(22) Filed: Jan. 28, 1999

(51) Int. Cl.⁷ .................................................. A61M 1/12
(52) U.S. Cl. ............................................. 600/16; 600/18
(58) Field of Search ................................. 600/16, 18

(56) References Cited

U.S. PATENT DOCUMENTS

| | | | |
|---|---|---|---|
| 3,568,659 | 3/1971 | Karnegis | 128/1 |
| 3,592,184 | * 7/1971 | Watkins | 600/16 |
| 3,802,551 | 4/1974 | Somers . | |
| 3,804,553 | 4/1974 | Hickey, Jr. . | |
| 4,019,830 | 4/1977 | Reid . | |
| 4,173,796 | 11/1979 | Jarvik | 3/1.7 |
| 4,591,355 | 5/1986 | Hilse | 604/159 |
| 4,625,712 | 12/1986 | Wampler | 128/1 |
| 4,690,002 | 9/1987 | Hubbard et al. | 73/861.25 |
| 4,697,574 | 10/1987 | Karcher et al. | 128/1 |
| 4,704,121 | 11/1987 | Moise | 623/3 |
| 4,753,221 | 6/1988 | Kensey et al. | 128/1 |
| 4,763,032 | 8/1988 | Bramm et al. | 310/90.5 |
| 4,779,614 | 10/1988 | Moise | 600/16 |
| 4,785,795 | 11/1988 | Singh | 600/18 |
| 4,817,586 | 4/1989 | Wampler . | |
| 4,846,152 | 7/1989 | Wampler et al. | 600/16 |
| 4,895,557 | 1/1990 | Moise et al. | 600/16 |
| 4,906,229 | 3/1990 | Wampler | 600/16 |
| 4,908,012 | 3/1990 | Moise et al. | 600/16 |
| 4,944,722 | * 7/1990 | Carriker et al. | 600/16 |
| 4,957,504 | 9/1990 | Chardack . | |
| 4,964,864 | 10/1990 | Summers et al. | 623/3 |
| 4,969,865 | 11/1990 | Hwang et al. . | |
| 4,984,972 | 1/1991 | Clausen et al. | 417/420 |
| 4,989,609 | 2/1991 | Smith et al. | 128/661.08 |
| 4,993,418 | 2/1991 | Weaver et al. | 128/661.08 |

(List continued on next page.)

FOREIGN PATENT DOCUMENTS

WO 92/02263  2/1992 (WO) .
WO 94/09835  5/1994 (WO) .

OTHER PUBLICATIONS publication, "Treatment of Cardiogenic Shock With the Hemopump Left Ventricular Assist Device", ©1991 by The Society of Thoracic Surgeons, pp. 506–513.
publication, "The Valvo–Pump: An Axial, Nonpulsatile Blood Pump", Mitamura et al., pp. M510–M512.
"Thermo Cardiosystems Acquires Nimbus Medical, Inc.", http://www.prnewswire.com/cgi–bin/stories.pl?ACCT= 105&STORY=/www/story/45711, 1998 PR Newswire .
"Thermo Cardiosystems Inc.", http://www.thermo.com/sub-sid/tca.html, 1998 Thermo Electron Corporation.

Primary Examiner—Carl H. Layno
(74) Attorney, Agent, or Firm—Burns, Doane, Swecker & Mathis, LLP

(57) ABSTRACT

A blood pump comprising a pump mechanism having an outer sleeve, an inner sleeve, and an impeller. The pump mechanism is movable between a closed and preferably retracted position wherein one or both of an inlet port and an outlet port are sealed by the inner and/or outer sleeve for inserting the pump mechanism into the heart, and an open and preferably extended position wherein the inlet and outlet ports are open to allow the impeller to pump blood through the ports. The pump mechanism preferably retracts so that it has less length and is more readily maneuvered when it is in its closed position. Also disclosed are a bearing portion received within a cap of the impeller with a flow of lubricating liquid between the bearing portion and cap, and a method of using the pump.

32 Claims, 8 Drawing Sheets

U.S. PATENT DOCUMENTS

| | | | |
|---|---|---|---|
| 4,994,078 | 2/1991 | Jarvik | 623/3 |
| 5,011,469 | 4/1991 | Buckberg et al. | 604/4 |
| 5,040,944 | 8/1991 | Cook . | |
| 5,061,256 | 10/1991 | Wampler | 604/280 |
| 5,092,879 | 3/1992 | Jarvik . | |
| 5,098,256 | 3/1992 | Smith . | |
| 5,112,349 | 5/1992 | Summers et al. . | |
| 5,133,870 | 7/1992 | Heidenreich . | |
| 5,139,391 | 8/1992 | Carrouset . | |
| 5,147,388 | 9/1992 | Yamazaki . | |
| 5,163,910 * | 11/1992 | Schwartz et al. | 604/151 |
| 5,176,619 | 1/1993 | Segalowitz . | |
| 5,211,546 | 5/1993 | Isaacson et al. . | |
| 5,275,580 | 1/1994 | Yamazaki . | |
| 5,290,227 | 3/1994 | Pasque . | |
| 5,299,938 | 4/1994 | Waltho . | |
| 5,354,288 | 10/1994 | Cosgrove et al. . | |
| 5,370,509 | 12/1994 | Golding et al. . | |
| 5,376,114 | 12/1994 | Jarvik . | |
| 5,399,074 | 3/1995 | Nose et al. . | |
| 5,527,159 | 6/1996 | Bozeman, Jr. et al. | 417/45 |
| 5,588,812 | 12/1996 | Taylor et al. . | |
| 5,603,337 | 2/1997 | Jarvik . | |
| 5,613,935 | 3/1997 | Jarvik . | |
| 5,616,137 | 4/1997 | Lindsay . | |
| 5,643,226 | 7/1997 | Cosgrove et al. . | |
| 5,685,865 | 11/1997 | Cosgrove et al. . | |
| 5,692,882 | 12/1997 | Bozeman, Jr. et al. . | |
| 5,695,471 | 12/1997 | Wampler . | |
| 5,707,218 | 1/1998 | Maher et al. . | |
| 5,738,626 | 4/1998 | Jarvik . | |
| 5,755,784 | 5/1998 | Jarvik . | |
| 5,776,190 | 7/1998 | Jarvik . | |
| 5,817,586 | 10/1998 | Harada et al. . | |
| 5,824,070 | 10/1998 | Jarvik . | |
| 5,840,070 | 11/1998 | Wampler . | |
| 5,851,174 | 12/1998 | Jarvik et al. . | |
| 6,132,364 * | 10/2000 | Rottenberg et al. | 600/16 |

* cited by examiner

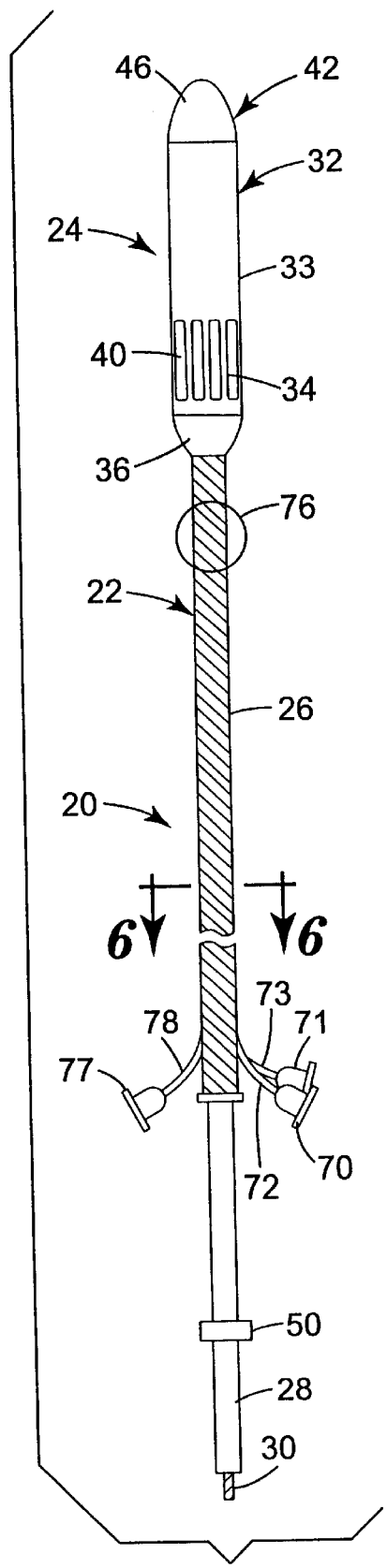
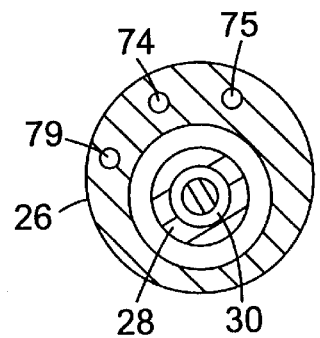
Fig. 6
Fig. 5

BLOOD PUMP

TECHNICAL FIELD

This invention relates to an intravascular blood pump, and in particular to pump adapted to be inserted into the apex of the heart, and alternatively to a pump adapted to be inserted via the aorta into the heart.

BACKGROUND OF THE INVENTION

In recent years great advancements have been made in the field of cardiac surgery. Surgical procedures to repair the heart or the heart's own blood supply are now frequently performed. One of the best known is the procedure called coronary artery bypass grafting, in which blood vessels taken from other parts of the patient's body are used to replace those portions of the coronary artery that have been damaged by disease. During such surgery it is necessary to take over the heart's function temporarily, either through a total bypass where the blood is pumped and oxygenated externally, or by the use of an intravascular blood pump.

Intravascular blood pumps are known that have a drive section integral to them, such as the one disclosed in U.S. Pat. Nos. 5,147,388 and 5,275,580. Others are intended to by powered by a remote power source via e.g. a drive shaft or cable, such as the ones disclosed in U.S. Pat. Nos. 4,625,712; 4,846,152; 4,964,864 and 5,112,349.

It is known to insert intravascular pumps into the heart through the vascular tree, via e.g. the femoral artery and the aorta. See, e.g., U.S. Pat. Nos. 4,625,712; 4,846,152 and 4,944,722. This placement suffers from the disadvantage that the aortic valve of the heart must be entered "backwards", i.e. against its natural flow direction. Great care must therefore be taken to avoid damage to the thin flaps of tissue that form the valve.

It is also known to insert intravascular blood pumps directly into the heart, piercing the heart wall at the heart's apex. See, e.g., U.S. Pat. Nos. 5,147,388; 5,275,580; 5,376,114; 5,755,784 and 5,776,190. Two problems arise with respect to the use of intravascular blood pumps that are inserted at the apex. First, such devices tend to be long and stiff, and it is difficult to maneuver the pump into position relative to the heart's internal structures. Second, the heart normally has some pressure within it, and blood tends to be forced backwards through the pump to spurt out into the open at some time during the insertion when the pump's outlet is within the heart and the pump's inlet is still outside the heart.

There has also been interest in a left atrial approach. This approach involves cutting a slit into the top of the heart into the left atrium, and threading the pump through the mitral valve into position on both sides of the aortic valve. Alternatively, this approach might involve threading the pump into the left atrium via a pulmonary vein.

SUMMARY OF THE INVENTION

The invention provides a blood pump having inlet and outlet ports, at least one of which can be opened or closed to fluid flow so that the blood pump can be inserted into the heart with the port closed, and the port can be opened to allow pumping blood. If the pump is being inserted via the apex of the heart, for example, the closed port restricts or prevents loss of blood or spurting of blood through the inlet port as the blood pump is inserted into position.

In one aspect of the invention, the intravascular blood pump generally comprises a driver, and a pump mechanism. The pump mechanism comprises inner and outer sleeves in sliding interengagement, and an impeller mounted within at least one of the inner and outer sleeves. One of the inner and outer sleeves includes a port, and the other of the inner and outer sleeves is movable relative to the port between a first position sealing the port and a second position wherein the port is open. The impeller is operatively connected to the driver to rotate the impeller to pump fluid through the port.

Preferably, the pump mechanism of the blood pump includes two portions that move axially with respect to each other after the pump mechanism has been inserted through the apex of the heart. Therefore, the blood pump can be moved into position while it is short or more readily maneuvered, for example, the blood pump can be positioned adjacent the aortic valve while it is short. Then once positioned, as one portion slides forward with respect to the other, the pump mechanism's outlet extends forward and opens, and its inlet, which had been sealed during the insertion, opens as well.

Alternatively, the inlet and/or outlet ports can be opened or closed via rotation, for example, by rotating one portion relative to another.

The invention may be considered as an intravascular blood pump having a cable assembly and a pump mechanism attached to that cable assembly. The cable assembly includes an outer sheath, an inner sheath partially enclosed within the outer sheath, and a drive cable partially enclosed within the inner sheath. The pump mechanism an outer sleeve, an inner sleeve, and an impeller. The inner sleeve has a vent for admitting the patient's blood into the pump mechanism, and is attached to the outer sheath of the cable assembly. The inner sleeve is in sliding engagement with the outer sleeve, and is attached to the inner sheath of the cable assembly. The impeller is mounted within the inner sleeve, and is attached to the drive cable. Assembled in such a manner, the pump mechanism is movable between a retracted position wherein the port is sealed by the inner sleeve, and an extended position wherein the port is open to admit blood to the impeller.

In preferred embodiments there is a locking mechanism attached to the inner sheath and adapted to engage the outer sheath so that the pump mechanism can be locked in the extended position while the intravascular blood pump is residing within the patient after insertion by the surgeon. Conveniently, the attachment between the inner sheath and the inner sleeve will be accomplished by a support member. Also conveniently, a distal member will be attached to the inner sleeve in a position adjacent and distal of the impeller for the purposes of providing a protective tip and improving the flow characteristics of the blood in that area.

While the intravascular blood pump of the present invention is particularly adapted for apical insertion, it will be clear that if the impeller is reversed, the invention can be used for insertion into the heart via the aortic valve. Many of the pump's desirable characteristics will still be available to the practitioner in such a mode.

In another aspect of the invention, the intravascular blood pump generally comprises a sheath having a flange and an internal lumen, and a drive cable partially enclosed within the internal lumen of the sheath. The sheath comprises a bearing portion generally adjacent the flange. The bearing has an end, at least one slot extending substantially between the flange and the end, and a channel along the end of the bearing portion providing fluid communication between the internal lumen and the slot. An impeller is mounted on the drive cable so that the impeller is rotated when the drive cable rotates. The impeller has a cap receiving the bearing portion of the sheath. The cap slideably engages the end of the bearing portion for rotation relative to the bearing portion. The cap has a flange disposed adjacent but not contacting the flange of the sheath to form a gap permitting the escape of fluid from the layer of fluid between the cap and bearing portion. Means, such as a reservoir of fluid, is provided for introducing a flow of fluid into the lumen of the sheath so that the flow of fluid passes through the slot to provide a layer of fluid between the cap and the bearing portion.

Most preferably, the bearing includes a plurality of longitudinally extending slots substantially equally spaced apart along the bearing portion, and a plurality of channels are provided along the end of the bearing portion to allowing fluid communication between the internal lumen and plurality of slots.

In yet another aspect of the invention, the intravascular blood pump generally comprises a pump housing having a central axis, and an inlet and an outlet defining upstream and downstream directions. An inlet flow straightener is provided within the housing downstream of the inlet for aligning blood entering the pump housing via the inlet with the central axis. An impeller is provided within the housing downstream of the inlet flow straightener, the impeller being mounted for rotation to pump blood from the inlet to the outlet. An outlet flow straightener is provided within the housing downstream of the impeller. The outlet flow straightener includes vanes extending substantially from the impeller substantially to the outlet, the vanes curving from a relatively radial orientation with respect to the central axis to a relatively axial orientation with respect to the central axis to decrease the circumferential component of the velocity of the blood before the blood exists the outlet.

Preferably, the pump housing is generally cylindrical, the outlet extends generally circumferentially around the pump housing, and the pump housing forms a generally conical or frustoconical structure adjacent the outlet opening to encourage radially outward flow of blood through the outlet. Also, preferably, the inlet comprises a plurality of inlet openings spaced radially apart along the pump housing. This helps avoid blockage of the inlet by the heart wall if the inlet is brought close to the heart wall.

Conveniently, a drive cable is operatively connected to the impeller to rotate the impeller, and the inlet flow straightener including a passageway through which the drive cable extends to operatively connect to the impeller.

These and other features will be pointed out hereinafter.

BRIEF DESCRIPTION OF THE DRAWING

The invention will be further described with reference to the drawing wherein corresponding reference characters indicate corresponding parts throughout the several views of the drawing, and wherein:

FIG. 5 is a side view of an alternate embodiment of the intravascular blood pump having optional passages for the conducting of fluids towards or away from the pump mechanism during use;

FIG. 6 is a cross-section view taken along section lines 6—6 in FIG. 5;

DETAILED DESCRIPTION OF PREFERRED EMBODIMENTS

Figure 1:
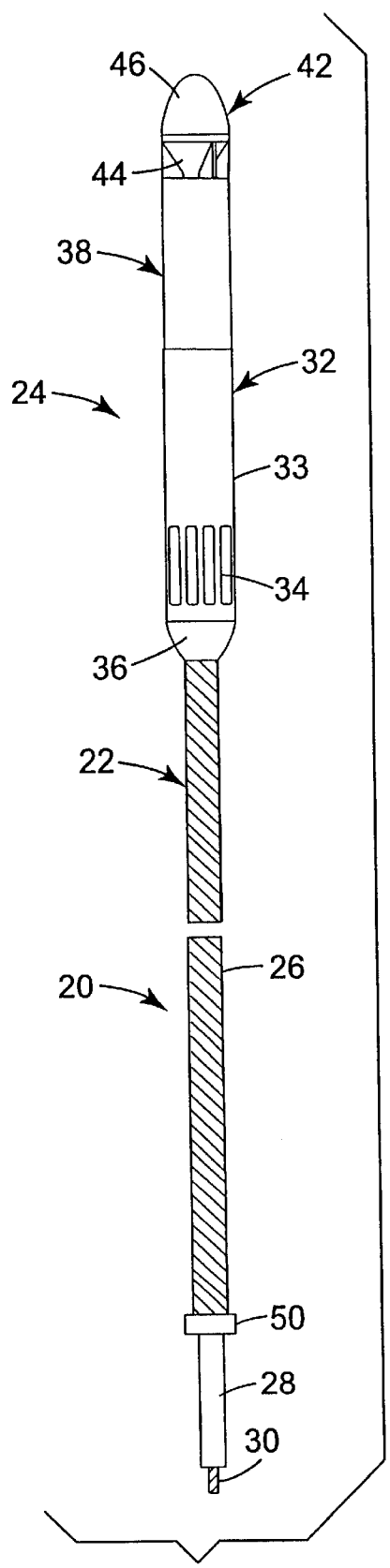
FIG. 1 is a side view of an intravascular blood pump according to the present invention in its extended position.

Referring now to FIG. 1, a side view of intravascular blood pump 20 is illustrated in its extended position. The intravascular blood pump 20 includes a cable assembly 22 and a pump mechanism 24. The cable assembly 22 has an outer sheath 26, an inner sheath 28 partially enclosed within the outer sheath, and a drive cable 30 partially enclosed within the inner sheath. The pump mechanism 24 includes an outer sleeve 32 including an outer sleeve wall 33 having a first or proximal port 34 (preferably an inlet port). The outer sleeve 32 is attached to the outer sheath 26 of the cable assembly 22; conveniently this is accomplished by a hub 36 having a smooth surface to facilitate the removal of the pump mechanism 24 from the patient's vasculature.

The pump mechanism 24 also includes an inner sleeve 38 that is in sliding engagement with the outer sleeve 32. The inner sleeve 38 has an inner sleeve wall 40 and preferably ends in a distal member 42 attached to the inner sleeve wall 40. The distal member 42 conveniently includes a vane portion 44 to promote a desirable flow pattern in the outflowing blood, and a tip portion 46 that has a smooth surface to facilitate the insertion of the pump mechanism 24 into the patient's vasculature. The vane portion 44 preferably includes vanes that curve from a relatively radially outwardly extending orientation from adjacent the impeller to a relatively axial orientation generally adjacent the downstream edge of the outlet.

Preferably, the tip portion 46 constitutes a dilator tip that allows insertion through small incisions in heart tissue. For example, the tip portion 46 may have a generally conical and/or beveled configuration to facilitate insertion. The dilator tip portion 46 may be formed of metal (e.g., stainless steel), plastic or a compliant elastomer. Particularly with an elastomeric tip portion 46, it is contemplated that an insertion/retaining plug (not shown) could extend axially from the tip portion 46 to hold the dilator tip portion 46 in position in the pump (e.g., to hold it to the vane portion 44). It is also contemplated that the distal vane portion 44 and the dilator tip portion 46 could be formed, e.g., molded, as one integral part as opposed to two parts fastened together.

When the pump mechanism 24 is in the extended position as illustrated in FIGS. 1, 3, 4c and 7, it has a second or distal port 48 adjacent the distal member 42, or to expressing this differently, the second or distal port 48 is opened when the pump mechanism 24 is extended. The second port 48 is preferably the outlet port.

The first or proximal port 34 preferably comprises a plurality of openings or slots (also 34) spaced apart radially along the outer sleeve 32. The preferred opening slits 34 preferably extend in the axial or longitudinal direction. This preferred arrangement involving a plurality of spaced apart openings is particularly desired for use as an inlet port 34 since it helps avoid blockage of the port 34 if the port is brought close to the heart wall. The second port 48 preferably extends completely circumferentially adjacent the distal end of the inner sleeve 38, and defines an annular opening (also 48) between the distal tip portion 42 and the inner sleeve 38. When the inner sleeve 38 is advanced distally relative to the outer sleeve 32, the inner sleeve 38 unblocks the proximal port 34, and the outer sleeve 32 uncovers the distal port 48.

A locking mechanism 50 is provided, attached to the inner sheath 28 and adapted to engage the outer sheath 26 for locking the pump mechanism 24 in the extended position during use. For example, the locking mechanism 50 may by formed by interlocking threaded members that can be turned to lock the pump mechanism 24 in the extended position. Other locking mechanisms may also be employed, such as for example, spring-arm type locking mechanisms, over-center locking mechanisms and bayonet-style locking mechanisms. In the case of a pump mechanism that opens and closes at least one port by moving one sleeve axially relative to the other sleeve, any suitable locking mechanism that prevents such axial movement or translation may be employed.

As used herein, the terms "proximal" and "distal" or variants thereof refer to the opposite directions axially of the pump 20. The distal member 42 defines the distal end of the pump 20, and the opposite direction along the pump 20 is the proximal direction.

As used herein, the term "inlet port" and "outlet port" refer to the port intended to be used as an inlet or outlet in the particular application of the pump. The first port 34 is the more proximally located port, and in the preferred embodiment is an "inlet" port. This arrangement is used when the pump is inserted into the patient's heart via the apex of the heart. In the alternative design, the more proximally-located port would be the "outlet" port since the alternative design involves feeding the pump into the heart from the other direction, e.g., via the aorta. The terms "distal port", "proximal port", "first port" or "second port" are used when the meaning is not to be limited to an inlet or outlet.

As used herein, "relative" when used in connection with movement of one part relative to another means that either part may actually move relative to the other part, e.g., a fixed part can move relative to a movable part. The terms "a", "an" and "the", as used herein, do not exclude the plural, whereas the terms "a single" or "the single" exclude the plural.

The terms "downstream" and "upstream" are defined relative to the intended travel of blood from the inlet to the outlet. The term "central axis" with respect to the pump housing (i.e., the inner and outer sleeves, tip, etc.) means the axis defined by the generally cylindrical inner and outer sleeves.

Figure 2:
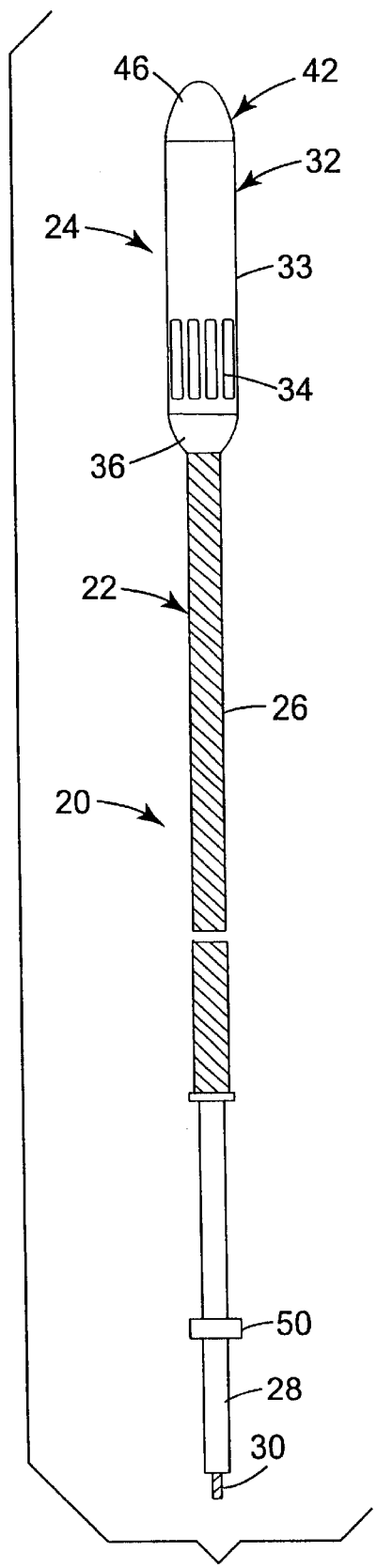
FIG. 2 is a side view of the intravascular blood pump of FIG. 1 in its retracted position.

Referring now to FIG. 2, the intravascular blood pump 20 of FIG. 1 is seen in side view in a retracted position. The outer sheath 26 has been moved in the direction of arrow 52 relative to inner sheath 28. The second port 48 is closed since the distal member 42 has been pulled up tight against the end of inner sleeve wall 40, and the first port 34 is also closed, blocked by the surface of inner sleeve wall 40.

Although longitudinal motion between the sleeves is considered preferred for the purposes of opening the ports and arraying the pump for use after insertion, it will be appreciated that the intravascular blood pump 24 could be constructed so that these purposes could be accomplished by rotary motion instead. For example, the pump could be designed so that the first and second ports could be opened or closed by rotating the sleeves relative to one another. More generally, one could state that the inner and outer sheaths are a preferred embodiment of a controller for the two sleeves, allowing them to be conveniently manipulated.

Figure 3:
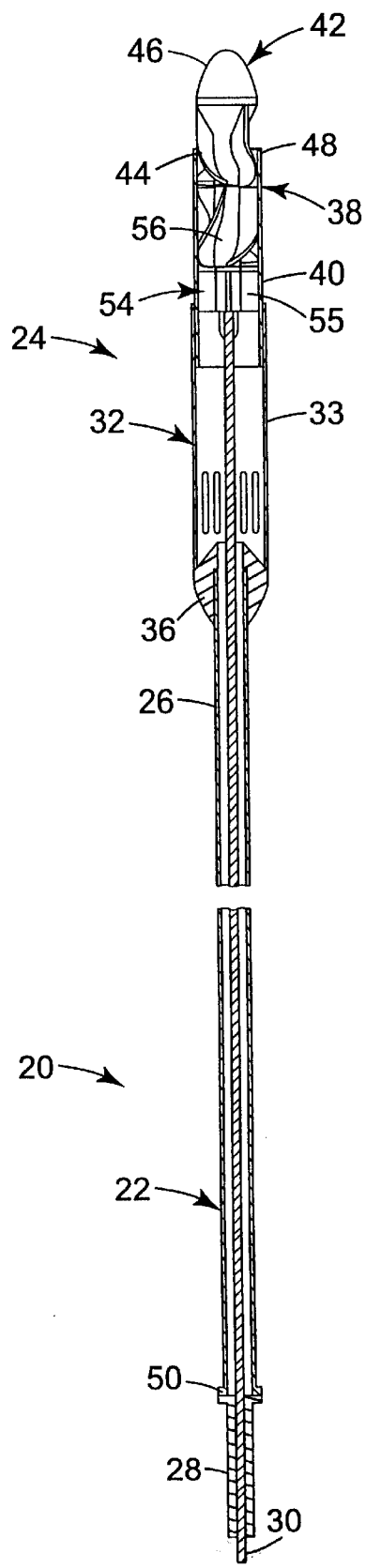
FIG. 3 is a partial cross-section side view of the intravascular blood pump in the extended position of FIG. 1.

Referring now to FIG. 3, the intravascular blood pump 20 of FIG. 1 is seen once again in its extended position, but this time in partial cross section view. In this view it can be seen that the outer sleeve 32 includes a support member 54 that which is attached to the inner sheath 28. Besides providing a structural function, the support member 54 has vanes 55 that straighten the flow of blood for better hydrodynamics through the pump mechanism 24. An impeller 56 is mounted within the inner sleeve 38 and is attached to the drive cable 30.

Figure 4A:
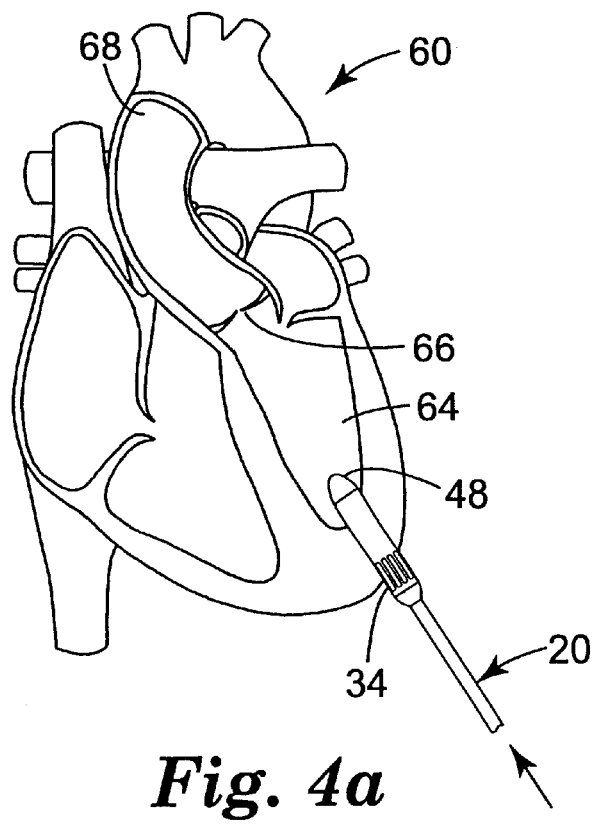
FIG. 4a is a cross-section view of a human heart as an intravascular blood pump according to FIG. 1 is being inserted into the apex.

Referring now to FIG. 4a, a cross-section view of a human heart 60 is illustrated. In this view, the intravascular blood pump 20 is being inserted into the apex 62 of the heart in order to assist or supplant the normal pumping action of the left ventricle 64. To accomplish this, the intravascular blood pump 20 must pump blood from the left ventricle 64 past the aortic valve 66 and into the ascending aorta 68. At the moment depicted in FIG. 4a, the second port 48 of the intravascular blood pump 20 is within the left ventricle 64, and the first port 34 is outside the heart 60. Since the intravascular blood pump 20 is inserted in its retracted position, the first port 34 and the second port 48 are closed to help block the flow of blood backwards through the pump. Without the feature of closing one or both ports during insertion as provided by this invention, blood would tend to flow backwards through the pump and into the surgical site, since there is typically some pressure within the left ventricle 64.

Figure 4B:
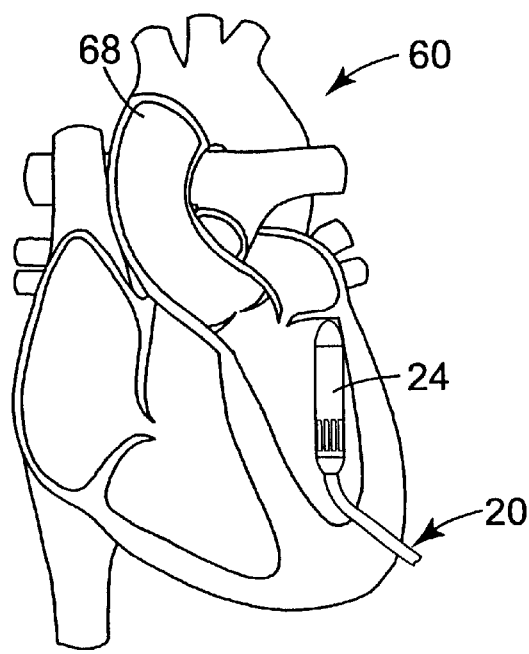
FIG. 4b is similar to the view of FIG. 4a, except that the intravascular blood pump is being maneuvered into position.

Referring now to FIG. 4b, the insertion is continued, and the intravascular blood pump 20 is being maneuvered into position. Another advantage of the preferred embodiment of the present invention can now be appreciated. In FIG. 4b, the intravascular blood pump 20 is not proceeding in the proper direction and must be pulled backwards a bit in order to reorient it. Since the pump mechanism 24 is shorter in length when it is in its retracted state, it is easier to maneuver in close quarters within the heart 60.

Figure 4C:
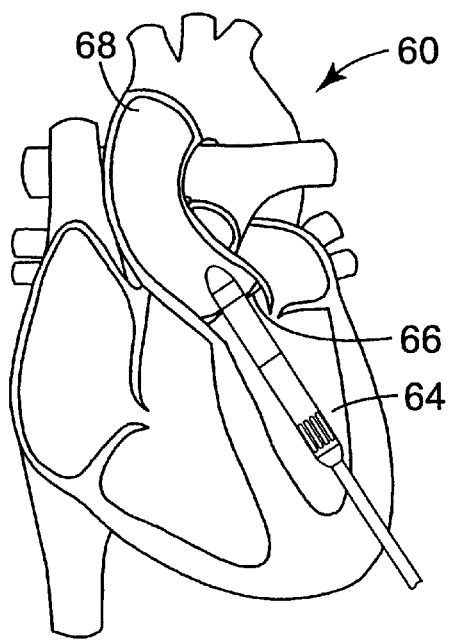
FIG. 4c is similar to the view of FIG. 4a, except that the intravascular blood pump has been located in a proper position for operation and is in its extended position.

Referring now to FIG. 4c, the intravascular blood pump 20 has been located in a proper position for operation and is in its extended position. When optimally placed, the first port 34 and the second port 48 are open and on opposite sides of the aortic valve 66.

Figure 4D:
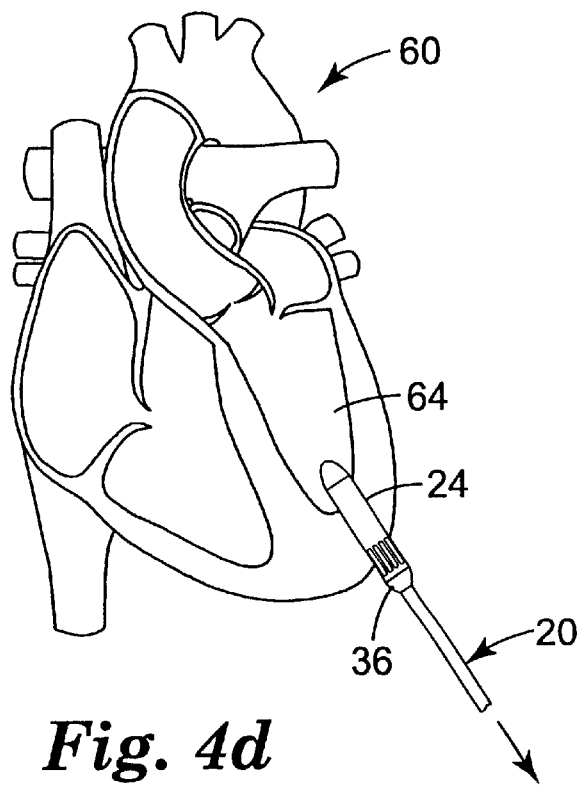
FIG. 4d is similar to the view of FIG. 4a, except that the intravascular blood pump is being withdrawn from the heart.

Referring now to FIG. 4d, the intravascular blood pump 20 is depicted being withdrawn from the heart. The smooth walls of the hub 36 facilitate the withdrawal of the pump mechanism 24. Once more the pump mechanism 24 is in its retracted state to seal the first port 34 and the second port 48 to prevent or at least restrict blood leakage through the pump mechanism 24.

Referring now to FIG. 5, a side view of an alternate embodiment of the intravascular blood pump 20 is illustrated. In that it is sometimes useful to introduce fluid material through the pump mechanism 24, e.g. heparinized saline to reduce any tendency to clot formation, or to remove fluid material through the pump mechanism, e.g. a blood sample for analysis, the depicted alternate embodiment includes optional passages for these purposes. Fluid connectors 70 and 71 are provided for connecting tubes 72 and 73 respectively to auxiliary equipment such as a syringe, a drip bag, or a sample-collecting vessel.

In FIG. 6, internal passageways 74 and 75, which connect with tubes 72 and 73 respectively, continue within the wall of outer sheath 26 for the purpose of conducting fluids towards or away from the pump mechanism 24 during the use of the intravascular blood pump 20.

In some embodiments it will be convenient to provide an inflatable balloon 76 that can be deflated for insertion, and then inflated while the pump mechanism 24 is within the heart using fluid connector 77, tube 78 and passageway 79. The cable assembly 22 can then be withdrawn slightly, drawing the balloon 76 up against the inside wall of the heart and helping to reduce any leakage of blood back through the surgical incision.

Figure 7:
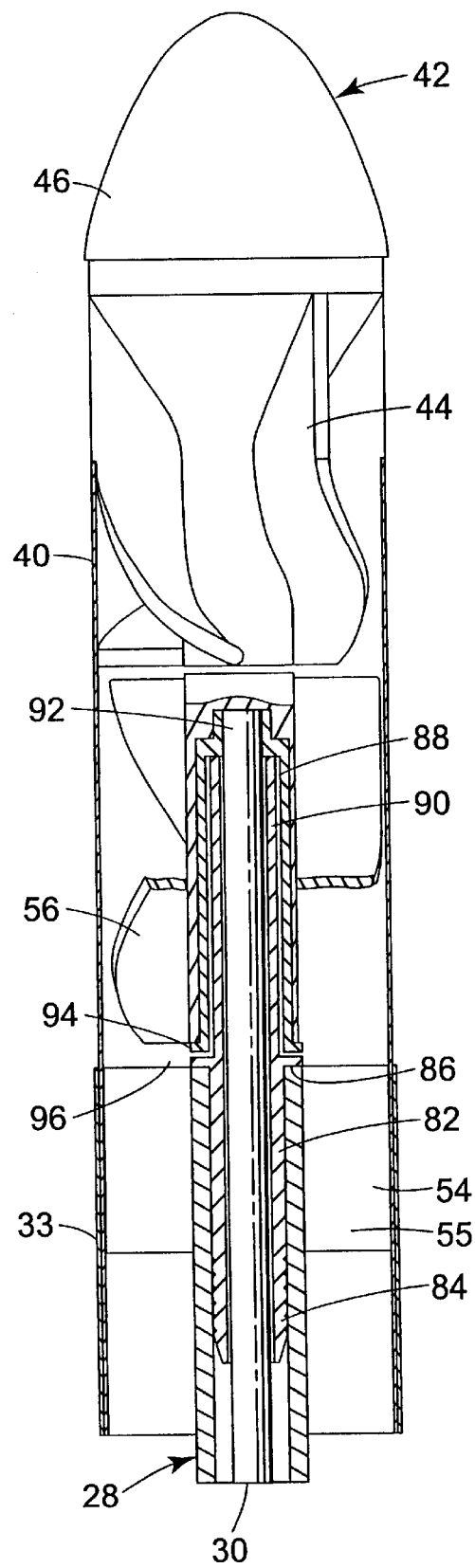
FIG. 7 is a detail cross-section view of a portion of the pump mechanism so as to show preferred embodiments of connection and bearing mechanisms.

Referring now to FIG. 7, a detail cross-section view of a portion of the pump mechanism 24 is illustrated so as to show preferred embodiments of connection and bearing mechanisms. Inner sheath 28 is connected to a spindle 82, conveniently by means of a threaded or barbed section 84. A flange 86 helps to capture the support member 54 in place. A cap 88, attached to the impeller 56, is intended to ride over and to spin around a bearing portion 90 of the spindle 82. The drive cable 30 is attached to the upper end 92 of the cap 88, conveniently by for example welding, soldering, or adhesive bonding. At its lower end, the cap 88 has a flange 94 of its own, and the parts are dimensioned and assembled so that there is a gap 96 between flange 86 on the spindle 82 and the flange 94 on the cap 88. It is currently considered preferred that the gap 96 be about 0.005 to 0.010 inch (0.125 to 0.250 mm) in width.

Figure 8:
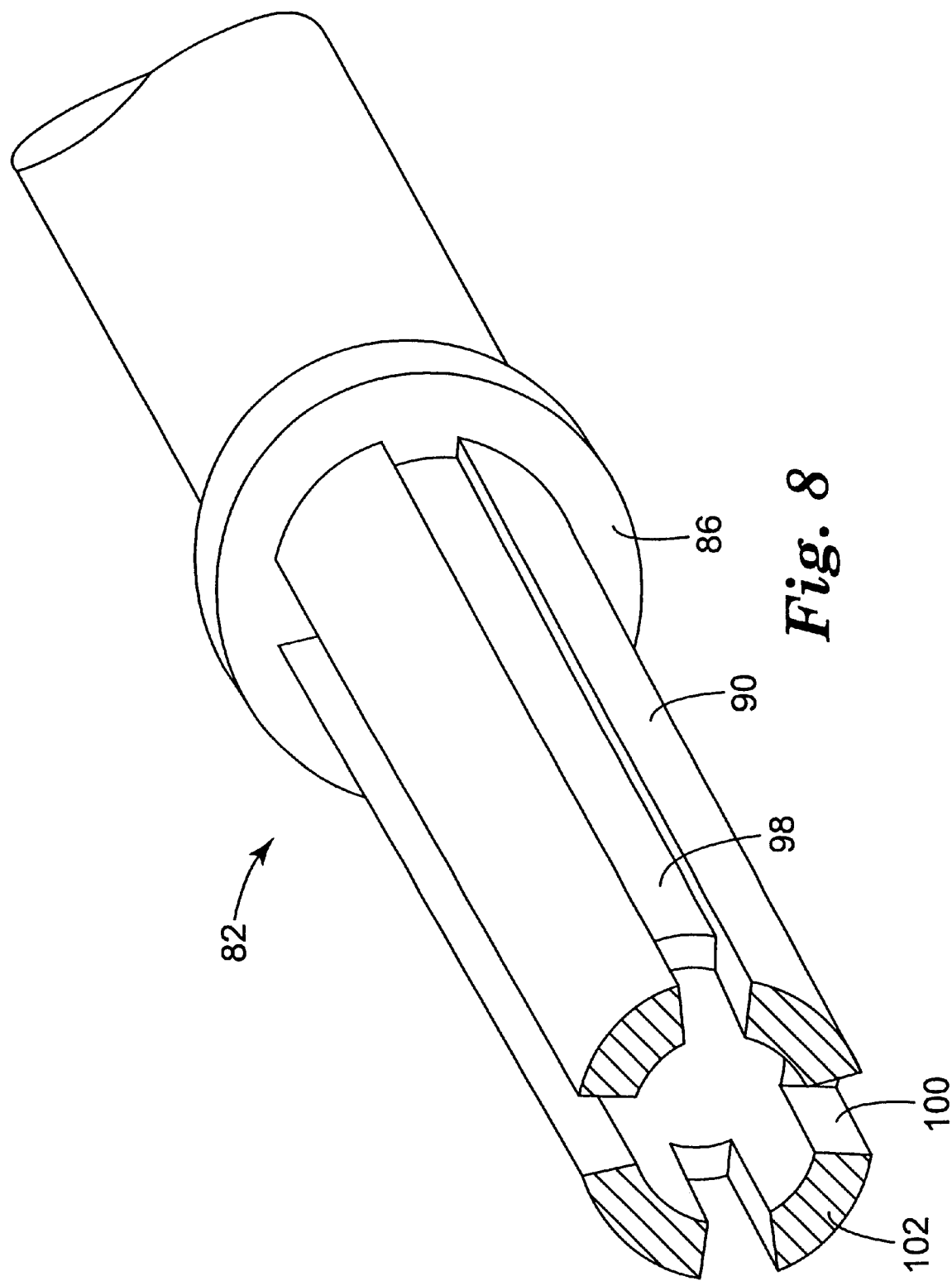
FIG. 8 is a detail perspective view of the bearing portion of the spindle.

The gap 96 provides a fluid bearing system. Referring now to FIG. 8, a detail perspective view of the bearing portion 90 of the spindle 82. One or more slots 98, conveniently four, are milled on the outside of the bearing portion 90, and each slot 98 ends adjacent a channel 100. Each channel 100 extends radially outwardly from the internal lumen to a slot 98 along the distal end 102 of the bearing portion 90 of the spindle 82. The distal end 102 provides a thrust bearing surface for the impeller. Most preferably, the slots 98 extend longitudinally along the bearing portion 90 and are substantially equally spaced apart, for example, four slots 98 equally spaced apart by 90 degree intervals.

In preferred embodiments, a flow of liquid, conveniently saline solution, is introduced under light pressure into the lumen of the inner sheath 28. This flow then exits the inner sheath 28 through the channels 100 and into the slots 98. The rate of fluid flow is adjusted so that the cap 88 rides on a thin layer of this fluid between the cap and the bearing portion 90. For example, the rate of fluid flow may be adjusted with a conventional roller clamp (not shown) of the type used with IV lines and the fluid may be provided by a flexible reservoir or bag of saline solution. The fluid flows out through the gap 96, and is drawn and diluted into the blood flow by the impeller 56.

While radially extending channels 100 are presently considered preferred, the artisan will perceive that there are other mechanical expedients that permit the requisite flow of fluid, e.g. small holes drilled within the slots 98 connecting them with the interior lumen of the bearing portion 90.

Figure 9:
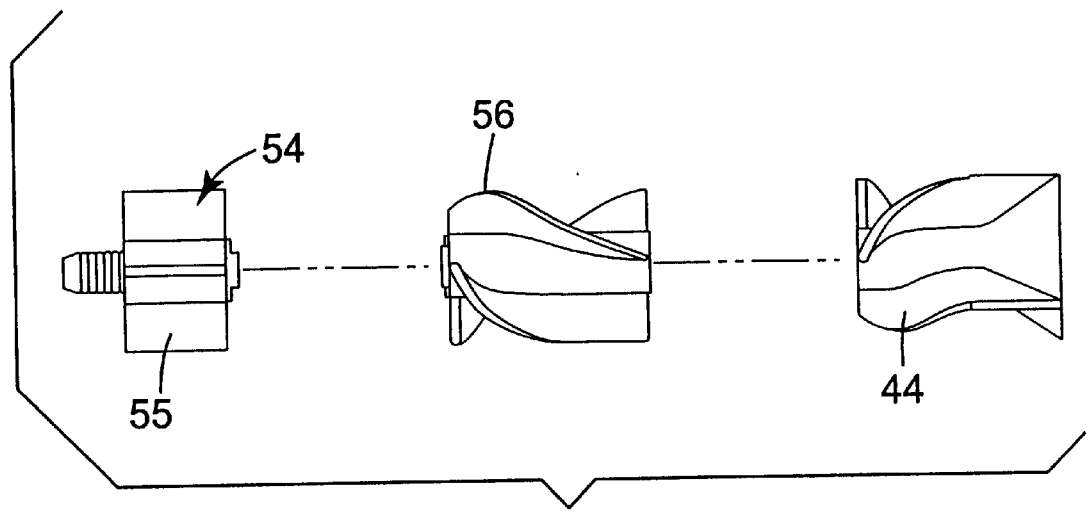
FIGS. 9 and 9a are exploded views of the main fluid handling components of the pump mechanism, FIG. 9 depicting the standard configuration adapted for apical insertion, FIG. 9a being an alternate embodiment adapted for insertion into the heart via the aortic valve.
Figure 9A:
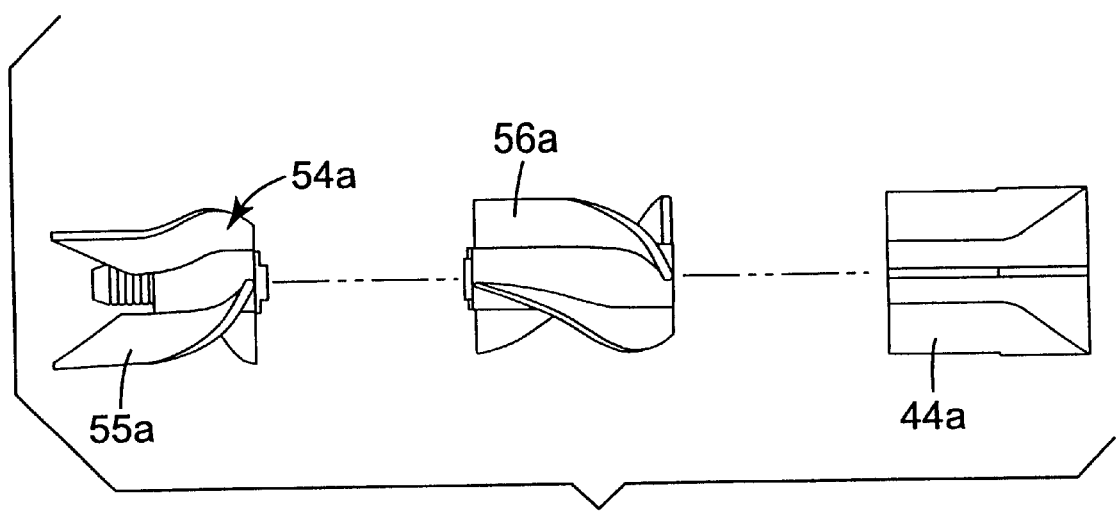

FIG. 9 illustrates an exploded view of the main fluid handling components of the pump mechanism 24 as above described, namely the support member 54, the impeller 56 and the vane portion 44 of the distal member. FIG. 9 can be contrasted with FIG. 9a, which is an alternate embodiment in which the pump mechanism is adapted for insertion into the heart via the aortic valve. In FIG. 9, the vanes 55 on the support member 54 are adapted to straighten the flow at the inlet end of impeller 56. At the outlet end of impeller 56, the vane portion 44 of the distal member is adapted to diffuse the flow of blood and to reduce its angular momentum with minimum damage to the blood cells. In contrast, in FIG. 9a, the vane portion 44a on the distal member is adapted to straighten the flow at the inlet end of a reverse acting impeller 56a. At the outlet end of reverse acting impeller 56a, the vanes 55a of the alternate support member 54a is adapted to diffuse the flow of blood.

U.S. Pat. Nos. 5,354,288; 5,616,137; 5,643,226 and 5,685,865 disclose various low velocity or fluid-diffusing catheters, and are incorporated herein by reference with respect to preferred embodiments of the outlet and the vane portion adjacent the outlet.

The outer sleeve wall 33 and the inner sleeve wall 40 are conveniently constructed of thin stainless steel tubing; a thickness of 0.005 inch (0.125 mm) is considered suitable. Conveniently, the intravascular blood pump 20 will be operated in conjunction with some means to rotate the drive cable. The artisan will perceive that there are numerous devices available for clamping to and rotating the drive cable; electrical and pneumatic motors are considered to be particularly suitable. A mag-lev drive, e.g. a drive of the type commercially available from Sulzer of Winterhur, Switzerland; Calnetix, Torrance, Calif. (URL: http://www.calnetix.com); or RMB-Mecos, Groton, Conn. (URL: http://www.rmb-ch.com/GUI/GB_1.html), are also contemplated as being suitable.

Magnetic drive units of this type are preferred because the allow both axial and rotational control of the drive cable, and because they can be easy to use, since the driven magnet attached to the drive cable merely needs to be inserted into the drive magnet assembly. In addition, axial control of the cable is particularly desirable if the pump is being used in the aorta insertion configuration, in which the impeller tends to want to move distally as it pushed blood in the proximal direction. The axial control of the cable can be used to help resist this force.

Drive speeds of between about 10,000 to 25,000 revolutions per minute are considered to be suitable in order to move between about 2 to 4 liters of blood per minute. A pressure head of between about 60 to 100 mm Hg should be maintained.

In that it is desirable that the sheaths be kink-resistant in order to be threaded into the vasculature, it is preferred to construct these parts from a flexible polymeric material. A nylon/polyurethane coextrusion, with nylon facing the lumen, polyurethane facing the exterior, and an internal diameter of 0.050 inches (1.27 mm), is presently considered preferred. A multi-stranded stainless steel cable is considered preferred for use as the drive cable. In particular, a wrapped, multi-stranded cable with three strands helically wrapped together in one direction forming a core and four to six strands helically wrapped in the opposite direction forming a jacket, the combined assembly having a diameter of about 0.040 inch (1.0 mm), is presently considered preferred. Such a construction has been fabricated by Suhner Manufacturing, Inc. of Rome, Ga., USA (Web address: http://www.suhnerusa.com).

The outer winding of the cable strands can form a type of Archimedes screw, which tends to pump saline along the cable. This feature can be employed to help pump saline along the cable in the desired distal direction, or alternatively in the proximal direction if the winding direction is reversed relative to the direction of rotation of the cable. In one preferred embodiment, the cable is coated with plastic (e.g., polyimide) to reduce or eliminate this pumping action and friction, dampen vibration or contain debris. It will be appreciated that such a coating may also facilitate priming the cable assembly.

Also, preferably, the length of the cable is adjustable and the cable includes a coupler along its length to permit changing the drive magnet portion without removing the pump from a patient's heart. A coupler can provide the mechanism for changing the length by allowing some fine adjustment, such as by a threaded means, and by allowing a section of intermediate cable to be provided to increase the length more substantially.

Various techniques may be employed to prime the pump before it is used. For example, the pump may be primed with saline before inserting it into the heart. In addition, saline may be flowed through the cable/sheath assembly to drive air from the assembly. Alternatively, a vacuum might be drawn to pull blood into the pump.

A fiber optic doppler flow sensor may also be employed in connection with this pump. U.S. Pat. Nos. 4,690,002; 4,989,609 and 4,993,418 disclose various features of a doppler flow measuring system, and are incorporated herein by reference.

It is also contemplated that a septum or plug could be sutured to the apex of the heart. For example, a generally self-sealing, pre-slit septum or plug could be sutured to the apex to provide a kind of port into the heart.

It is further contemplated that the pump could be used with a guide wire to facilitate advancing the pump into position. For example, a removable guidewire could pass through the pump housing between the distal tip and the distal end of the cable sheath. Such a guidewire could be offset from the central axis so that it passes between the vanes of the outlet flow straightener, impeller and inlet flow straightener.

Also contemplated as alternatives are the use of one or two inflatable balloons to seal against the heart wall adjacent the incisions through the apex of the heart. One inflatable balloon could be provided to seal against the inside of the heart wall, which would also help to hold the blood pump in position away from the heart wall. Preferably, a second inflatable balloon would also be employed to seal against the outside of the heart wall.

Another contemplated embodiment is to provide an expandable inlet basket on the inner sleeve so that the inlet basket expands when the outer sleeve is extended distally. This inlet basket helps ensure that heart tissue is well separated from the inlet opening.

It is further contemplated that embodiments that are designed for insertion via the aorta include a snap bearing connecting the impeller to the bearing portion. Such a snap bearing would include an annular channel and a mating ridge or the like that would tend to resist distal movement of the impeller relative to the bearing portion notwithstanding the distal force of blood being pumped in the proximal direction by the impeller.

As various changes could be made in the above constructions and methods without departing from the scope of the invention as defined in the claims, it is intended that all matter contained in the above description or shown in the accompanying drawings be interpreted as illustrative and not in a limiting sense.

What is claimed is:

1. An intravascular blood pump, comprising:
    a cable assembly having:
        an outer sheath;
        an inner sheath partially enclosed within the outer sheath; and
        a drive cable partially enclosed within the inner sheath; and
    a pump mechanism comprising
        an outer sleeve having a port therein and being attached to the outer sheath;
        an inner sleeve in sliding engagement with the outer sleeve, the inner sleeve being attached to the inner sheath; and
        an impeller mounted within at least one of the inner and outer sleeves, the impeller being attached to the drive cable;
        the inner and outer sleeves being movable relative to one another between:
            a retracted position wherein the port is sealed by the inner sleeve; and
            an extended position wherein the port is open to permit fluid communication through the port with the impeller.

2. The intravascular blood pump according to claim 1 further comprising a locking mechanism attached to one of the inner sheath or the outer sheath and adapted to engage the other sheath for locking the pump mechanism in the extended position.

3. The intravascular blood pump according to claim 1 wherein the inner sleeve further comprises:
    a support member attached to the inner sheath proximally of the impeller, and
    a distal member adjacent the impeller distally of the impeller.

4. The intravascular blood pump according to claim 3 wherein the port constitutes a first port, the pump mechanism further having a second port adjacent the distal member, the second port being open when the pump mechanism is in the extended position and is closed by the outer sleeve when the pump mechanism is in the retracted position.

5. The intravascular blood pump according to claim 3 wherein
    the inner sheath is attached to the support member by means of a spindle, the spindle having an interior lumen, a flange and a bearing portion, the bearing portion having at least one slot and at least one fluid connection between the interior lumen and the slot; and
    the impeller comprises a cap attached to the drive cable, the cap having a flange disposed adjacent the flange on the spindle;
    the blood pump further comprises means for introducing a flow of fluid into the inner sheath so that the flow of fluid passes through the slot so as to provide a layer of fluid between the cap and the bearing portion of the spindle.

6. The intravascular blood pump according to claim 5 wherein the fluid connection between the interior lumen and the slot is a cut-down portion adjacent the distal end of the bearing portion.

7. The intravascular blood pump according to claim 1 further comprising:

an inflatable balloon mounted on the outer sheath adjacent the pump mechanism; and means for inflating the balloon.

8. A method of providing blood circulation for a surgical patient, comprising the steps of:
(a) providing an intravascular blood pump, comprising:
a cable assembly having:
an outer sheath;
an inner sheath partially enclosed within the outer sheath; and
a drive cable partially enclosed within the inner sheath; and
a pump mechanism comprising
an outer sleeve having a first port therein and being attached to the outer sheath;
an inner sleeve in sliding engagement with the outer sleeve, the inner sleeve being attached to the inner sheath and at least partly defining a second port distally located relative to the first port; and
an impeller mounted within the inner sleeve, the impeller being attached to the drive cable;
the pump mechanism being movable between a retracted position wherein at least one of the first and second ports is sealed by one of the inner and outer sleeves, and an extended position wherein the first and second ports are open to permit fluid communication with the impeller;
(b) making an incision at the apex of the heart;
(c) while maintaining the intravascular blood pump in its retracted position to close at least one of the first and second ports, inserting the blood pump through the incision;
(d) placing the intravascular blood pump in it extended position and causing a portion of the inner sleeve to pass through one of the heart valves so that the second port is on the opposite side of the heart valve relative to the first port; and
(e) rotating the drive cable to thereby rotate the impeller to circulate blood.

9. The method according to claim 8 further comprising the step of locking the pump mechanism in the extended position.

10. The method according to claim 8 wherein the both the first and second ports are closed when the pump mechanism is in its retracted position.

11. The method according to claim 8 wherein the intravascular blood pump further comprises an inflatable balloon mounted on the outer sheath adjacent the pump mechanism;
the intravascular blood pump is inserted through the incision with the balloon a deflated condition;
the method further comprises the steps of
inflating the balloon after the inserting of the intravascular blood pump; and
withdrawing the cable assembly sufficiently to bring the balloon in contact with the inner wall of the heart.

12. An intravascular blood pump, comprising:
a driver; and
a pump mechanism comprising:
inner and outer sleeves in sliding interengagement, one of the inner and outer sleeves including a port, and the other of the inner and outer sleeves being movable relative to the port between a first position sealing the port and a second position wherein the port is open;
an impeller mounted within at least one of the inner and outer sleeves the impeller being operatively connected to the driver to rotate the impeller to pump fluid through the port; and
a controller operatively connected to the inner and outer sleeves to move them between the first and second positions.

13. The intravascular blood pump according to claim 12, wherein the driver comprises a drive cable, and the controller comprises at least one sheath enclosing the drive cable.

14. The intravascular blood pump according to claim 13 wherein the sheath is an inner sheath and wherein the controller further comprises an outer sheath, so that the inner sheath is partially enclosed within the outer sheath.

15. The intravascular blood pump according to claim 14 further comprising a locking mechanism attached to one of the inner sheath or the outer sheath and adapted to engage the other sheath for locking the pump mechanism in the second position.

16. The intravascular blood pump according to claim 14 wherein the inner sleeve further comprises:
a support member on the proximal side of the impeller, the inner sheath being attached to the support member
a distal member adjacent the impeller on the distal side of the impeller.

17. The intravascular blood pump according to claim 16 wherein the port constitutes a first port, the pump mechanism further having a second port adjacent the distal member that is open when the pump mechanism is in the second position and is closed when the pump mechanism is in the first position.

18. The intravascular blood pump according to claim 16 wherein
the inner sheath is attached to the support member by means of a spindle, the spindle having an interior lumen, a flange and a bearing portion, the bearing portion having at least one slot and at least one fluid connection between the interior lumen and the slot;
the impeller comprises a cap attached to the drive cable, the cap having a flange disposed adjacent the flange on the spindle; and
the blood pump further comprising means for introducing a flow of fluid into the inner sheath so that the flow of fluid passes through the slot so as to provide a layer of fluid between the cap and the bearing portion of the spindle.

19. The intravascular blood pump according to claim 18 wherein the fluid connection between the interior lumen and the slot is a cut-down portion adjacent the distal end of the bearing portion.

20. The intravascular blood pump according to claim 12 further comprising an inflatable balloon mounted on the outer sheath near the pump mechanism, and means for inflating the balloon.

21. An intravascular blood pump adapted to be inserted into a heart via the apex of the heart, the blood pump comprising:
a cable assembly having:
an outer sheath;
an inner sheath partially enclosed within the outer sheath; and
a drive cable partially enclosed within the inner sheath; and
a pump mechanism comprising:
an inner sleeve operatively connected to the inner sheath;
a distal member operatively connected to the inner sleeve and/or the inner sheath;

an outer sleeve having an inlet port therein, the outer sleeve being in sliding engagement with the inner sleeve and operatively connected to the outer sheath such that axial movement of the outer sheath relative to the inner sheath moves the outer sleeve axially relative to the inner sleeve between a closed position in which the inlet port is sealed by the inner sleeve and the outer sleeve sealingly engages the distal member; and an open position in which the inlet port is not sealed by the inner sleeve and the outer sleeve is spaced from the distal member to define an outlet port between the distal member and the outer sleeve; and an impeller mounted within at least one of the inner and outer sleeves, the impeller being operatively connected to the drive cable so that the impeller is rotated when the drive cable rotates.

22. The intravascular blood pump according to claim 21 further comprising a locking mechanism attached to one of the inner sheath or the outer sheath and adapted to engage the other sheath for locking the pump mechanism in the open position.

23. The intravascular blood pump according to claim 21 wherein the inner sleeve further comprises a support member and the inner sheath is attached to the support member.

24. The intravascular blood pump according to claim 23 wherein the inner sheath is attached to the support member by means of a spindle, the spindle having an interior lumen, a flange and a bearing portion, the bearing portion having at least one slot and at least one fluid connection between the interior lumen and the slot, and wherein the impeller comprises a cap attached to the drive cable, the cap having a flange disposed adjacent but not contacting the flange on the spindle.

25. The intravascular blood pump according to claim 24 further comprising means for introducing a flow of fluid into the inner sheath so that the flow of fluid passes through the slot so as to provide a layer of fluid between the cap and the bearing portion of the spindle.

26. The intravascular blood pump according to claim 21 further comprising an inflatable balloon mounted on the outer sheath near the pump mechanism, and means for inflating the balloon.

27. An intravascular blood pump comprising:

a sheath having a flange, the sheath comprising:
an internal lumen;
a bearing portion generally adjacent the flange, the bearing having:
an end;
at least one slot extending substantially between the flange and the end; and
at least one channel along the end of the bearing portion providing fluid communication between the internal lumen and the slot;

a drive cable partially enclosed within the internal lumen of the sheath;

an impeller mounted on the drive cable so that the impeller is rotated when the drive cable rotates, the impeller having a cap receiving the bearing portion of the sheath, the cap slideably engaging the end of the bearing portion for rotation relative to the bearing portion, the cap having a flange disposed adjacent but not contacting the flange of the sheath to form a gap permitting the escape of fluid from the layer of fluid between the cap and bearing portion to purge the gap of blood; and means for introducing a flow of fluid into the lumen of the sheath so that the flow of fluid passes through the slot to provide a layer of fluid between the cap and the bearing portion.

28. The intravascular blood pump according to claim 27 wherein the slot comprises a plurality of longitudinally extending slots substantially equally spaced apart along the bearing portion and the channel comprises a plurality of channels along the end of the bearing portion providing fluid communication between the internal lumen and plurality of slots.

29. The intravascular blood pump according to claim 27 wherein the pump includes a proximal inlet and distal outlet, and the force of blood being pumped by the impeller tends to drive the cap toward the end of the bearing portion.

30. An intravascular blood pump comprising:

a pump housing having a central axis, and an inlet and an outlet defining upstream and downstream directions;

an inlet flow straightener within the housing downstream of the inlet for aligning blood entering the pump housing via the inlet with the central axis;

an impeller within the housing downstream of the inlet flow straightener, the impeller being mounted for rotation to pump blood from the inlet to the outlet; and an outlet flow straightener within the housing downstream of the impeller, the outlet flow straightener including vanes extending substantially from the impeller substantially to the outlet, the vanes curving from a relatively radial orientation with respect to the central axis to a relatively axial orientation with respect to the central axis to decrease the circumferential component of the velocity of the blood before the blood exists the outlet;

wherein the pump housing is generally cylindrical, the outlet extends generally circumferentially around the pump housing, and the pump housing forms a generally conical or frustoconical structure adjacent the outlet opening to encourage radially outward flow of blood through the outlet.

31. The blood pump according to claim 30 wherein the inlet comprises a plurality of inlet openings spaced radially apart along the pump housing.

32. The blood pump according to claim 31 further comprising a drive cable operatively connected to the impeller to rotate the impeller, the inlet flow straightener including a passageway through which the drive cable extends to operatively connect to the impeller.

* * * * *